United States Patent [19]
Money et al.

[11] 4,453,162
[45] Jun. 5, 1984

[54] EFFICIENT AND FAST-SWITCHING TELEMETRY TRANSMITTER

[75] Inventors: David K. Money, Pennant Hills; Christopher N. Daly, Bilgola Plateau, both of Australia

[73] Assignee: Telectronics Pty. Ltd., Lane Cove, Australia

[21] Appl. No.: 376,276

[22] Filed: May 10, 1982

[51] Int. Cl.³ .................. G08C 19/00; A61N 1/00
[52] U.S. Cl. .................. 340/870.39; 128/419 PT; 128/903; 340/870.01; 340/870.07; 340/573; 455/127
[58] Field of Search ............ 340/870.39, 870.3, 870.1, 340/870.01, 825.5, 573, 870.07; 455/127, 343; 128/903, 419 PS, 419 PT; 320/DIG. 1

[56] References Cited
U.S. PATENT DOCUMENTS 3,949,388 4/1976 Fuller .................. 128/903
4,236,523 12/1980 Gruenenwald .......... 128/419 PT
4,281,664 8/1981 Duggan .................. 128/903

*Primary Examiner*—James J. Groody
*Attorney, Agent, or Firm*—Gottlieb, Rackman and Reisman

[57] ABSTRACT

A transmitter for a medical prosthesis which is highly efficient, and also permits rapid starting and stopping so that the same coil can be used for both transmission and reception without undue delays between the two modes of operation. During transmission, a tuned circuit, consisting of the coil and a capacitor, is pumped at a frequency equal to the resonant frequency. Transmission is concluded when almost all of the energy in the tuned circuit is in the form of a voltage across the capacitor and when the current through the inductor is approximately zero. This allows the inductor to be used immediately for reception. At the start of the next transmission cycle, the voltage which is maintained across the capacitor is used to initially energize the tuned circuit.

14 Claims, 3 Drawing Figures

EFFICIENT AND FAST-SWITCHING TELEMETRY TRANSMITTER

DESCRIPTION

This invention relates to telemetry transmitters, and more particularly to telemetry transmitters which are used in biomedical applications.

For many years now, conventional heart pacers have been provided with a programmable capability. An external programmer, operated by a physician, transmits coded pulses to a telemetry receiver inside the pacer case. Depending upon the parameter values selected by the physician, the pacer operation may be modified. In addition to changing the mode in which the pacer operates, such things as amplifier sensitivity, pacing rate, and pulse widths may be adjusted.

In more recent times, attention has been paid to the transmission of information in the reverse direction, that is, from the pacer or some other medical prosthesis to an external monitor. The medical prosthesis can thus transmit data about how it is operating and data from which the medical condition of the patient can be determined. For example, it has been proposed to have the pacer count the number of events of particular interest, e.g., the number of premature beats which have occurred subsequent to the last interrogation, and to so advise the physician by having the data transmitted from the pacer for display on an external monitor.

Telemetry systems of this type, in which information can be transmitted in both directions, have been known for many years, not only in biomedical systems but also in many others. However, there are certain problems which are peculiar to biomedical applications, which problems have not been completely solved. For one thing, many medical prostheses such as heart pacers are completely shielded in an hermetically-sealed metallic case. This means that the signal, in both directions, must pass through the case. To avoid excessive eddy current losses if the electromagnetic transmission itself is through the case, the rate of data transmission must be limited. In many systems, transmission in the two directions alternates. This is especially true where transmission from the pacer takes place only in response to an externally-generated interrogation command. Although protocols differ, it is quite common for the pacer to have to switch rapidly between transmitting and receiving modes of operation. The need for the pacer circuitry to rapidly switch between modes of operation is particularly important when the data rate is limited. Prior art biomedical telemetry systems of this type have not generally allowed the pacer to rapidly switch between transmitting and receiving modes of operation.

It is a general object of our invention to provide a telemetry transmitter which is capable of rapidly starting and stopping. By this is meant that if a burst of pulses is transmitted, as soon as the transmitter is turned on the pulses which are generated are of full amplitude so that the first few pulses in any sequence are not "wasted"; no extra time is required for orderly transmission to begin. It also means that upon cessation of the transmission of a pulse burst, immediate switching to the receive mode of operation is possible; the same coil used for transmission can be used immediately for reception without having to wait significantly for any circuits to settle down.

One of the most important factors to consider in the design of a medical prosthesis such as a heart pacer is that of power dissipation. A pacer battery should last for many years. Obviously, the additional functions of transmitting and receiving data require the expenditure of energy. So as not to deleteriously affect pacer life, it is very important that the telemetry system be as efficient as possible. It is the transmitter which presents the biggest problem when it comes to the dissipation of energy. Typically, a tuned circuit is used to control oscillations in the transmitting coil. At the end of any transmission sequence, energy is stored in the tuned circuit in the form of current which flows through the coil and charge which is stored on a capacitor. If this energy is allowed to dissipate, it is simply wasted. It would be highly desirable to conserve whatever energy is stored in the tuned circuit so that it is available for the next transmission sequence. Furthermore, whatever circuitry is employed to achieve this end should utilize CMOS transistors which are known for their low power dissipation (for which reason they are traditionally used in heart pacers and other medical prostheses).

It is another object of our invention to provide a highly efficient telemetry transmitter which, while permitting rapid starting and stopping of carrier bursts, also minimizes energy losses.

Briefly, in accordance with the principles of our invention, we provide a class C transmitter; as in the prior art, the transmitter consists of a tuned circuit which is pumped during each cycle of operation. At the end of a transmission sequence, however, the transmitter is turned off when the current through the coil is approximately zero, and essentially all of the energy stored in the tuned circuit is in the form of charge on the capacitor. Because there is almost no current through the coil, the receiver which is connected to the coil may begin to operate almost immediately, with the coil picking up any electromagnetic signal which is transmitted from an external device. During the receive mode of operation, the charge remains stored on the capacitor. At the start of another transmitting cycle, the capacitor is switched back into the tuned circuit at just the right time so that the initial charge on the capacitor can control a full-amplitude oscillatory cycle, with the tuned circuit being pumped briefly once during each cycle. In this manner, not only is a minimum of energy wasted, but the very first pulse which is transmitted is of full amplitude and at the conclusion of the last pulse the coil is ready to operate in a receive mode.

Further objects, features and advantages of our invention will become apparent upon consideration of the following detailed description in conjunction with the drawing, in which.

Figure 1:
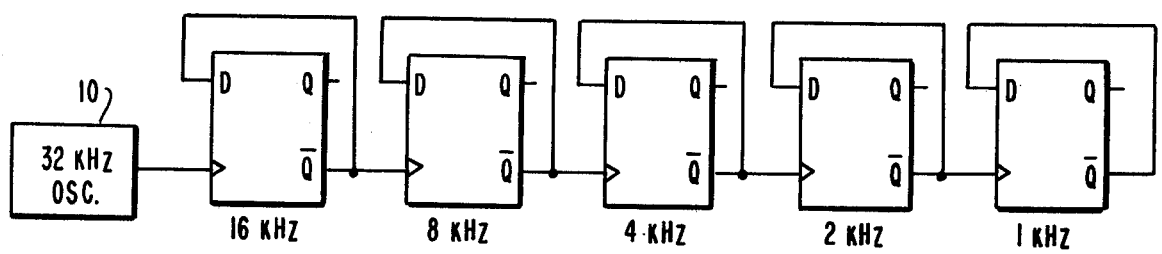
FIG. 1 depicts a source of clock signals for controlling the operation of the telemetry system of our invention.
Figure 2:
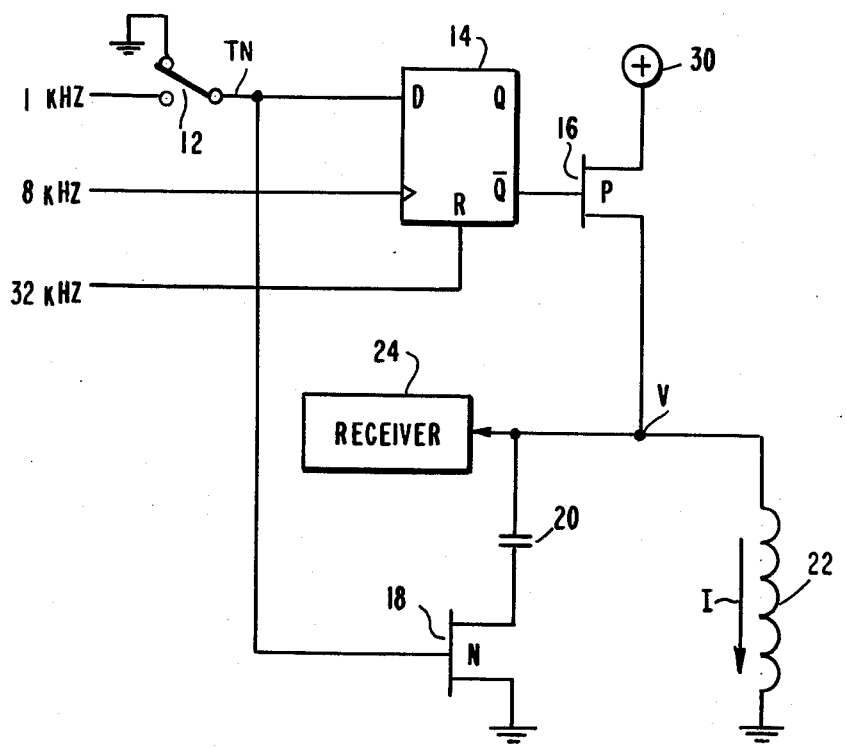
FIG. 2 depicts the illustrative embodiment of our invention.
Figure 3:
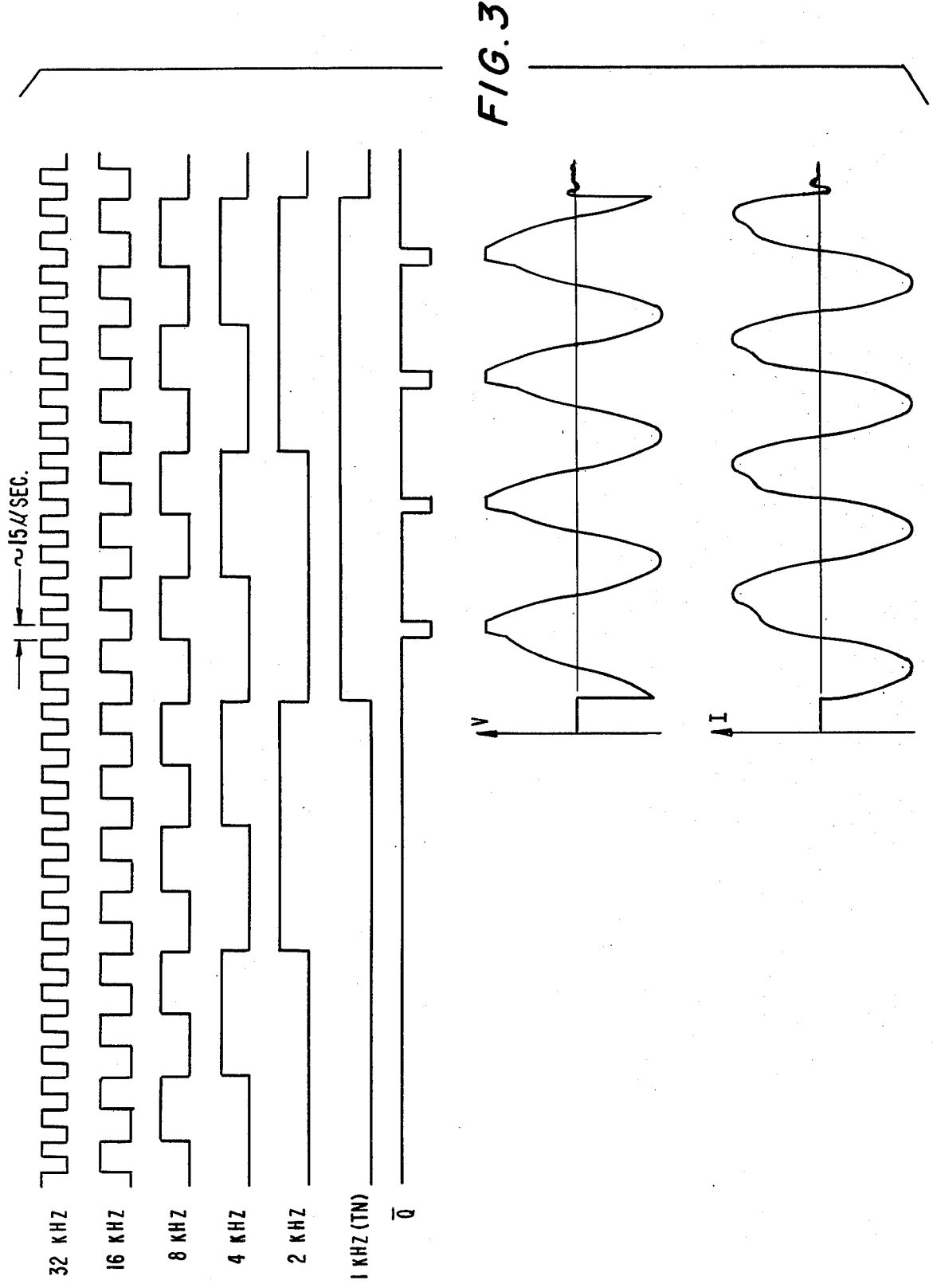
FIG. 3 depicts several waveforms which will be helpful in understanding the operation of the system of FIG. 2.

A typical heart pacer includes a titanium case. As described above, in order to reduce eddy currents, data must be transmitted through the case at relatively low rates. In the illustrative embodiment of our invention, a rate of 8 kHz is utilized. The basic clock for the system is a 32-kHz oscillator 10, as shown in FIG. 1. Five D-type flip-flops are utilized for dividing down the basic clock frequency (although the only clocks which are actually utilized in the system of FIG. 2 are the 1-kHz, 8-kHz and 32-kHz signals). Each flip-flop in FIG. 1 toggles on the rising edge of the waveform applied to its clock input. Each flip-flop operates as a divide-by-two counter because of the connection of its $\overline{Q}$ output to its D input, as is known in the art. The first six waveforms in FIG. 3 depict the 32-kHz clock signal and the five clock signals which are derived from it. Each of the 16-kHz through 1-kHz waveforms represents the signal at the Q output of the respective flip-flop. Since each flip-flop has its toggle input connected to the $\overline{Q}$ output of the preceding flip-flop, each flip-flop is toggled when the $\overline{Q}$ output of the preceding flip-flop goes high; this, in turn, means that each flip-flop toggles when the Q output of the preceding flip-flop goes low. It is for this reason that the 16-kHz through 1-kHz waveforms in FIG. 3 exhibit transitions when the waveform of the next higher clock frequency, corresponding to the preceding flip-flop, exhibits a falling edge.

The system of FIG. 2 includes a single D-type flip-flop 14 which is controlled by three of the clock signals. Two transistors are utilized, P-channel transistor 16 and N-channel transistor 18. The tuned circuit consists of capacitor 20 and coil 22. The voltage at the junction of the capacitor and the inductor is represented by the letter V, and the current through the coil is represented by the letter I. As the current reverses in direction at an 8-kHz rate, pulses are transmitted. Similarly, coil 22 picks up externally generated signals, with voltage V representing the received signal. Receiver 24 is shown only in block form inasmuch as it can be any conventional design. As described above, what is desired is a transmitter which can start and stop rapidly. As will become apparent below, as soon as a transmission cycle ceases, no current flows through the coil, and the receiver can almost immediately start operating on signals picked up by the coil.

Referring to the waveforms of FIG. 3, it will be noted that the 1-kHz waveform is indicated to also represent the TN signal. Switch 12 is simply a switch which is connected between the 1-kHz clock, and flip-flop 14 and transistor 18. The 1-kHz clock signal has an effect on the system only if switch 12 is closed (connected to the 1-kHz signal line). The only constraint on the operation of switch 12 is that it first close (when data is to be transmitted) while the 1-kHz clock signal is low, that it remain closed while the 1-kHz clock signal is high, and that the switch open only after the clock signal has gone low once again. As will become apparent below, a low potential applied to the D input of flip-flop 14 or to the gate of transistor 18 has no effect on the system operation. It is only when the D input of the flip-flop and the gate of the transistor are high that transmission takes place. Thus, as long as switch 12 is first closed before the 1-kHz clock pulse goes high and is opened only after the clock signal has gone low again, for all intents and purposes, the 1-kHz clock signal controls the transmission as though switch 12 were not even present. Whenever switch 12 is closed during the positive half of a 1-kHz clock cycle, it controls a four-cycle burst. If the switch remains open, a burst is not generated. While the switch is shown as being mechanical, it is to be understood that in actual practice an electronic switch is preferred, any of many standard switches being suitable.

Whenever the 8-kHz clock signal goes high, flip-flop 14 is toggled and it assumes a state which represents the potential at its D input. It will be noted from the waveforms of FIG. 3, that each positive transition in the 8-kHz clock signal which occurs while the TN signal is low has no effect on the state of flip-flop 14. After the flip-flop is first set in the 0 state, it remains in this state for as long as the D input is low in potential. Thus the $\overline{Q}$ output of the flip-flop remains high, as shown in the seventh waveform of FIG. 3. When the TN signal first goes high, the 8-kHz clock goes low. This has no effect on the state of the flip-flop; the device is toggled only when a positive step appears at its toggle input. It is when the 8-kHz clock signal next goes high that the state of the flip-flop is switched to a 1. At this time the $\overline{Q}$ output goes low, as shown in the seventh waveform in FIG. 3. This occurs on the falling edge of a 32-kHz clock signal. Approximately 15 microseconds later, the 32-kHz clock signal goes high. Since this clock signal is connected directly to the reset input of flip-flop 14, the flip-flop is immediately switched back to the 0 state, and the $\overline{Q}$ output goes high once again. Consequently, the overall result is that the $\overline{Q}$ output of the flip-flop exhibits a negative pulse which is approximately 15 microseconds in duration.

The same thing happens during each of the next three cycles of the 8-kHz clock signal. The rising edge of the fourth 8-kHz pulse during the time that the TN signal is high causes the $\overline{Q}$ output of flip-flop 14 to go low in the usual way. Approximately 15 microseconds later the $\overline{Q}$ output goes high again on the rising edge of the 32-kHz clock. At the falling edge of the TN clock, the D input of flip-flop goes low. Consequently, the next rising edge of the 8-kHz clock effects no change in the state of the flip-flop since it is already in the 0 state and it remains there.

It is the four negative pulses at the $\overline{Q}$ output of flip-flop 14 which control the transmitter operation.

Assuming that switch 12 is closed while the 1-kHz clock signal is low in potential (the required operation, as described above), the gate of transistor 18 is low in potential and this transistor is held off. Similarly, the $\overline{Q}$ output of flip-flop 14 is high in potential; since the $\overline{Q}$ output is connected to the gate of transistor 16, this transistor is also held off. It will be assumed that capacitor 20 is initially charged, with its lower terminal being positive in potential and its upper terminal being connected through coil 22 to ground. (The justification for these assumptions will become apparent below.) Transistor 16 is connected to a positive potential source 30, e.g., a battery. Neglecting potential drops across the two transistors, nearly the full source potential initially appears across capacitor 20.

The eighth waveform in FIG. 3 depicts potential V in the circuit of FIG. 2. At the start of the transmission sequence, the TN signal goes high and transistor 18 turns on. Transistor 16 is still off, however, and the net result of turning transistor 18 on is that capacitor 20 and coil 22 are connected in a closed circuit. The circuit starts to oscillate with current flowing up through coil 22. As soon as the lower terminal of the capacitor is grounded through transistor 18, since the battery potential still appears across the capacitor, potential V drops sharply as shown in FIG. 3.

The last waveform of FIG. 3 depicts the current through the coil. Initially, the coil current is zero. When the tuned circuit starts to oscillate on the rising edge of the TN waveform, the current which flows through the coil is in a direction opposite to the "positive" direction depicted in FIG. 2, so that the initial current in the last waveform of FIG. 3 is negative.

The capacitor and inductor are tuned to 8 kHz. It will be noted that the 8-kHz clock signal goes low when the TN signal goes high. After one-half cycle of the 8-kHz clock has progressed, one-half cycle of tuned circuit oscillation has taken place. Consequently, by the time the 8-kHz clock signal goes high, potential V is at the highest potential that it would otherwise reach, and the current through the coil has gone through its negative peak and has returned to zero preparatory to a change in direction. It is just at this time that the $\overline{Q}$ output of flip-flop 14 goes low for 15 microseconds to turn on transistor 16. At this time, there is a rapid rise in potential V due to the connection of the junction of the capacitor and the inductor through transistor 16 to the positive supply. The transistor is held on for about 15 microseconds, and thus potential V remains at the potential of the power supply (neglecting the drop across the transistor) until the $\overline{Q}$ output goes high to turn off the transistor. At this time the tuned circuit starts to oscillate again. Almost a full cycle takes place, and just when potential V nears a peak, transistor 16 conducts once again. To whatever extent the potential across the capacitor is no longer equal to the supply potential due to losses in the tuned circuit, the capacitor potential (potential V) is pumped up to the peak value. At the termination of the second 15-microsecond pumping pulse, the tuned circuit oscillates once again. This process continues until the capacitor has been pumped for the fourth time. At the end of the fourth pumping pulse, the tuned circuit oscillates once again. This time, transistor 18 is turned off in the middle of the cycle when the TN signal goes low. Consequently, the tuned circuit can no longer oscillate because the capacitor and the inductor are not connected to each other in a closed circuit. The top of the capacitor is returned to ground through the inductor and, while the capacitor remains charged, potential V rises to ground; the bottom of the capacitor remains floating. The energy stored in the capacitor is utilized to energize the tuned circuit at the start of the next transmission sequence.

The current through coil 22 can be analyzed in a similar manner. As described above, until the first pulse at the $\overline{Q}$ output of the flip-flop is generated, the current waveform goes through one-half cycle. There is some distortion in the current waveform when transistor 16 turns on and the current through the coil is pumped in the positive direction. Thus the current waveform exhibits a sharp rise at the start of each $\overline{Q}$ pulse. At the termination of each pumping pulse, the current continues to oscillate and it reaches a peak just when the voltage across the capacitor is zero. Toward the end of the pulsed operation, when the oscillator is interrupted with the turning off of transistor 18, the voltage across the capacitor is near its maximum negative value. The inductor current is approaching a zero value at this time and ceases to flow almost instantaneously.

Thus not only is the inductor current very close to zero when the transmission ceases, but the upper terminal of the capacitor is grounded, thus justifying the original assumption that nearly the peak voltage appears across capacitor 20 with the upper terminal, or potential V, being at ground potential. It is thus apparent that the receiver can almost immediately begin to function with no interference from the transmitting circuit. For all intents and purposes, the voltage across capacitor 20 is irrelevant during reception because its lower terminal is floating due to the fact that transistor 18 does not conduct. There is no current flowing through the coil and any externally generated signals which are picked up by the coil result in a potential V which can be operated upon by the receiver. As long as the external transmission ceases before switch 12 is closed and potential V returns to ground potential, a sharp negative step is exhibited by potential V at the start of the next transmission cycle.

It is important to analyze the voltage and current waveforms in greater detail. During transmission, transistor 18 is held on and transistor 16 is driven by narrow pulses at the resonant frequency of the tuned coil (or at a frequency which is at least approximately equal to the resonant frequency). To terminate a pulse burst, transistor 18 is turned off when potential V is almost at its most negative value, and the current through the coil is almost zero. The current through the coil is not quite zero at this time because the last half cycle of current oscillation is not a complete half cycle; the oscillation cannot begin until the last 15-microsecond pulse terminates and this necessarily means that the current through the coil has not decayed to zero by the time transistor 18 turns off. Nevertheless, the current through the coil rapidly decays to zero; oscillations are set up at the resonant frequency of the coil and any stray capacitance around it. The large damping which is to be expected causes the current to decay rapidly, as shown in the last waveform of FIG. 3. In actuality, there is very little energy which dissipates in this manner because almost all of the energy originally stored in the tuned circuit is now in the form of charge on the capacitor, leaving very little to be dissipated in the coil in the form of losses.

When transistor 18 turns off and interrupts the tuned circuit operation, nearly the full battery potential appears across capacitor 20, with the bottom terminal of the capacitor being positive with respect to the upper terminal. As soon as the current through the coil ceases and the upper terminal of the capacitor rises to ground potential (as shown at the rightmost end of the voltage waveform in FIG. 3), the bottom terminal of capacitor 20 floats. The potential across the capacitor remains, except for minor losses due to leakage, until transistor 18 turns on once again. When this happens, the bottom terminal of the capacitor is returned to ground through the transistor. Since almost the full battery potential is still stored across the capacitor, the upper terminal goes negative relative to ground, as indicated by the sharp drop in potential V at the start of a pulse burst. It is the energy which is thus stored in the capacitor which allows virtually instantaneous build-up of the first pulse in the burst.

It should be noted that with the clocks used in the illustrative embodiment of the invention, in each one-millisecond cycle of the 1-kHz clock 0.5 milliseconds are available for transmission, during which four pulses may be transmitted in a burst, and 0.5 milliseconds are available during which receiver 24 can operate on an externally-transmitted signal.

Referring to the voltage waveform, as described above, at the start of a transmission cycle voltage V abruptly to a level approximately equal to minus the supply voltage. A full half-cycle of the 8-kHz clock progresses before the first 15-microsecond current pumping pulse occurs. Consequently, the tuned circuit goes through a complete half-cycle of operation, and voltage V is at a peak of the naturally oscillating signal when the $\overline{Q}$ output of flip-flop 14 is first pulsed low. Voltage V is then held at the potential of the battery for fifteen microseconds. This is one-quarter of the way into a positive half-cycle of the 8-kHz clock. The next pumping pulse occurs at the start of the next positive half-cycle of the 8-kHz clock. This means that the tuned circuit does not actually go through one complete cycle of operation from the time that transistor 16 turns off and the time that it turns on once again. Instead, it goes through only seven-eigths of a complete cycle. It is for this reason that voltage V at the start of the second pulse at the $\overline{Q}$ of the flip-flop does not reach the same peak which is reached by the time the first pumping pulse occurs. Similar remarks apply to the remaining pulses in the burst. This is of no moment, however, because the pumping pulse raises voltage V to the full potential of the battery. The last three pulses are all phase shifted relative to the first by one-eighth of an 8-kHz clock cycle due to the delay introduced by the pumping pulses relative to the first half cycle of oscillation. This is of no moment whatsoever as long as the external receiver is capable of responding to a burst of four pulses which occur at approximately an 8-kHz rate. It is also of interest to note that the voltage which remains across capacitor 20 at the termination of a transmission sequence is not quite equal to the full potential of the battery. This is because the oscillation of the tuned circuit ceases abruptly on the falling edge of the 1-kHz clock when transistor 18 turns off, and the last half cycle of oscillation starts at the trailing edge of the $\overline{Q}$ pulse which is one-eighth of the way into an 8-kHz clock cycle. This means that voltage V has not quite reached a maximum negative peak by the time oscillations abruptly cease. It is for this reason that the starting and terminating voltages are shown in the voltage waveform of FIG. 3 as being slightly less in magnitude than the peak voltages which are reached during normal oscillations.

With reference to the current waveform of FIG. 3, it will be noted that the current goes through a half cycle of operation and returns to zero at just that time when voltage V has reached a peak during the natural oscillation, as is to be expected since the first half cycle of oscillation is complete. During the first 15-microsecond pumping pulse, the current through the coil increases in the positive direction beyond the increase which would occur due to a natural oscillation. At the termination of the pumping pulse, the current then increases at a rate less than that at which it would normally increase, the peak current being reached when the voltage waveform passes through zero. Thus there is some distortion in the current waveform. This is of no concern, however, since an ordinary external receiver responds to bursts of energy, and not to well defined pulses. Similar distortion is exhibited in each of the succeeding current pulses, when the current is positive and is increasing. It is to be noted that the current through the coil has not decreased to zero by the time transistor 18 is turned off. The current has not decreased to zero for precisely the same reason that voltage V has not reached a peak negative voltage by the time transistor 18 turns off. Although "perfect" operation could result by extending the positive half cycle of the 1-kHz waveform slightly—until the current reduced to zero and the voltage across the capacitor reached a negative peak, little is to be gained by the additional complexity; the energy which is thus wasted is insignificant and the voltage which remains across the capacitor is so large in magnitude that the first pulse is of almost full amplitude.

Although the system of FIG. 2 controls a burst of four pulses whenever switch 12 is closed, more sophisticated signalling schemes are possible. Our invention is directed to maximizing the efficiency of the transmitter and allowing rapid starting and stopping of transmission; many different coding schemes can be employed which utilize the same principles. For example, one possible coding scheme might comprise a form of amplitude modulation. To transmit a bit of value 0, switch 12 might be closed for one-and-a-half half cycles of the 1-kHz clock, with the switch closing just prior to the clock waveform going high, and then remaining closed while the clock waveform is high, while it is low for a half cycle, and then high for another half cycle. The two successive four-pulse bursts (separated by a 0.5-millisecond interval during which data reception takes place) could represent a bit of value 0. To transmit a bit of value 1, switch 12 might remain closed for only one half cycle of the 1-kHz clock. The absence of a second four-pulse burst following a first would represent a bit of value 1.

Similarly, a form of phase modulation could also be employed. In such a case, switch 12 might always be closed for one-and-a-half cycles of the 1-kHz clock, allowing two pulse bursts to occur. However, during the second pulse burst, the 8-kHz clock pulses might be delayed by a half cycle. Thus if the pulses in the two bursts are in phase with each other, a bit of one value might be represented, whereas if they are out of phase with each other a bit of opposite value might be represented. (With this kind of scheme, and in order not to have to change the phase of the 1-kHz clock, only three pulses might be generated in the second burst since delaying the first pumping pulse relative to the rising edge of the TN signal would not allow for four complete pulses to be generated.) In general, it is to be appreciated that many different coding schemes can be employed. That is why switch 12 is shown only symbolically in FIG. 2. The invention can be understood by considering the 1-kHz clock signal to be applied directly to the D input of flip-flop 14 and the gate of transistor 18 when they allowed to go high in order to control transmission. What is important for an understanding of the present invention is what takes place from beginning to end of any cycle during which a pulse burst is generated.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A signalling system comprising a transmitter tuned circuit having a capacitor and an inductor therein, means for selectively enabling and disabling said tuned circuit to oscillate, means for pumping said tuned circuit when it is enabled at a frequency which is at least approximately equal to the resonant frequency of said tuned circuit, and means for controlling the disabling of said tuned circuit following a previous enablement when approximately all of the energy stored therein is in the form of voltage across said capacitor and for maintaining and then utilizing the voltage across said capacitor to initially energize the tuned circuit when it is next enabled.

2. A signalling system in accordance with claim 1 further including a receiver connected to said inductor, said inductor functioning both to transmit radiation and to receive radiation from another source, said controlling means allowing said receiver to operate in conjunction with said inductor almost instantaneously when said tuned circuit is first disabled by controlling said tuned circuit to become disabled when the current flowing through said inductor as a result of the previous enablement of said tuned circuit has oscillated to a value of approximately zero.

3. A signalling system in accordance with claim 2 further including means for causing said enabling and disabling means to operate continuously so as to alternately enable and disable said tuned circuit, whereby periods of transmission and reception continuously alternate with each other.

4. A signalling system in accordance with claim 3 wherein the resonant frequency of said tuned circuit is such that transmission can take place through the metallic case of a medical prosthesis.

5. A signalling system in accordance with claim 4 wherein said receiver, said capacitor and said inductor are connected together at a common node, said enabling and disabling means is a first switching means for connecting the other ends of said capacitor and said inductor to each other, and said pumping means includes a source of potential and a second switching means for connecting said source of potential to said common node.

6. A signalling system in accordance with claim 5 wherein said source of potential is referenced to a ground level, said other end of said inductor is connected to said ground level, and said first switching means is connected between the other end of said capacitor and said ground level.

7. A signalling system in accordance with claim 6 wherein said first switching means closes while said second switching means is open, said second switching means thereafter periodically closing only briefly when the potential at said common node is approximately at a peak whose polarity is the same as that of said potential source due to the natural oscillation of said tuned circuit, and said first switching means opens while said second switching means is open and when the potential at said common node is approximately at a peak whose polarity is opposite to that of said potential source due to the natural oscillation of said tuned circuit.

8. A signalling system in accordance with claim 1 wherein the resonant frequency of said tuned circuit is such that transmission can take place through the metallic case of a medical prosthesis.

9. A signalling system in accordance with claim 1 wherein said receiver, said capacitor and said inductor are connected together at a common node, said enabling and disabling means is a first switching means for connecting the other ends of said capacitor and said inductor to each other, and said pumping means includes a source of potential and a second switching means for connecting said source of potential to said common node.

10. A signalling system in accordance with claim 9 wherein said source of potential is referenced to a ground level, said other end of said inductor is connected to said ground level, and said first switching means is connected between the other end of said capacitor and said ground level.

11. A signalling system in accordance with claim 10 wherein said first switching means closes while said second switching means is open, said second switching means thereafter periodically closing only briefly when the potential at said common node is approximately at a peak whose polarity is the same as that of said potential source due to the natural oscillation of said tuned circuit, and said first switching means opens while said second switching means is open and when the potential at said common node is approximately at a peak whose polarity is opposite to that of said potential source due to the natural oscillation of said tuned circuit.

12. A signalling system in accordance with claim 11 wherein the resonant frequency of said tuned circuit is such that transmission can take place through the metallic case of a medical prosthesis.

13. A signalling system in accordance with claim 11 further including a receiver connected to said inductor, said inductor functioning both to transmit radiation and to receive radiation from another source, said controlling means allowing said receiver to operate in conjunction with said inductor almost instantaneously when said tuned circuit is first disabled by controlling said tuned circuit to become disabled when the current flowing through said inductor as a result of the previous enablement of said tuned circuit has oscillated to a value of approximately zero.

14. A signalling system in accordance with claim 9 further including a receiver connected to said inductor, said inductor functioning both to transmit radiation and to receive radiation from another source, said controlling means allowing said receiver to operate in conjunction with said inductor almost instantaneously when said tuned circuit is first disabled by controlling said tuned circuit to become disabled when the current flowing through said inductor as a result of the previous enablement of said tuned circuit has oscillated to a value of approximately zero.

* * * * *